United States Patent

Möhring et al.

Patent Number: 5,811,087
Date of Patent: Sep. 22, 1998

[54] HAIR SHAMPOO

[75] Inventors: Hartmut Möhring, Seeheim-Jugenheim, Germany; Satoshi Onitsuka, Oyamashi, Japan; Bettina Schupp, Pfungstadt, Germany

[73] Assignee: KAO Corporation, Japan

[21] Appl. No.: 696,575

[22] Filed: Aug. 16, 1996

[30] Foreign Application Priority Data

Aug. 19, 1995 [DE] Germany .......... 195 30 550.7

[51] Int. Cl.⁶ .................. A61K 7/07; A61K 7/00
[52] U.S. Cl. .................. 424/70.19; 424/70.17; 424/70.15
[58] Field of Search ............ 424/70.28, 70.11, 424/70.19, 70.17, 70.1

[56] References Cited

U.S. PATENT DOCUMENTS 4,818,440 4/1989 Schäfer et al. .......... 252/596

FOREIGN PATENT DOCUMENTS 0671463 9/1995 European Pat. Off. .
9508614 3/1995 WIPO .

OTHER PUBLICATIONS

Zviak, The Science of Hair Care, pp. 121–125, 1986.
Derwent Ref. No. 94–061976/08; Jan. 24, 1995.

*Primary Examiner*—Sally Gardner-Lane
*Attorney, Agent, or Firm*—Londa and Traub LLP

[57] ABSTRACT

A conditioning aqueous hair shampoo composition having good lathering properties, an excellent conditioning effect and outstanding skin compatibility contains a) 1% to 25% by wt., of at least one alkyl amidoether carboxylic acid of the general formula I

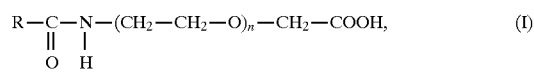

wherein R denotes an alkyl group having 8 to 18 carbon atoms, and n is a number between 1 and 10, and (or) the water-soluble salts thereof;

b) 1% to 25% by wt. of at least one anionic surfactant of the sulfate and (or) sulfonate type;

c) 0.1% to 10% by wt. of at least one compound selected from the group of $C_8$–$C_{18}$-acyl mono- and -dialkanolamides, surface-active betaines and sulfobetaines and (or) surface-active amine oxides; and d) 0.05% to 5% by wt. of at least one cationic polymer.

9 Claims, No Drawings

HAIR SHAMPOO

BACKGROUND OF THE INVENTION

This invention comprises a liquid aqueous hair shampoo composition providing good lathering properties upon application with water, having good skin compatibility, rendering the hair soft and pliable and providing it with volume, shine and improved wet and dry combability.

According to the invention, such a shampoo comprises, in an aqueous medium, a mixture of a) 1% to 25% by wt., preferably 5% to 20% by wt. of an alkyl amidoether carboxylic acid of formula I

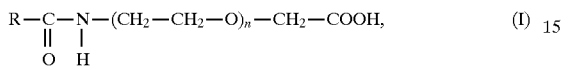

wherein R denotes an alkyl group having 8 to 18 carbon atoms, and n is a number between 1 and 10, and (or) the water-soluble salts thereof;

b) 1% to 25% by wt. of at least one anionic surfactant of the sulfate and (or) sulfonate type;

c) 0.1% to 10% by wt. of at least one compound selected from the group of $C_8$-$C_{18}$-acyl mono- and -dialkanolamides, surface-active betaines and sulfobetaines and (or) surface-active amine oxides; and d) 0.05% to 5% by wt. of at least one cationic polymer, all percentages calculated to the total shampoo composition.

R preferably presents an alkyl group bearing from 12 to 14 carbon atoms, and n is preferably a number from 2.5 to 5, particularly 3 to 4.

The proportion of anionic surfactant preferably consists of about 25% to 50% by wt. of the alkyl amidoether carboxylic acid according to formula I. Suitable water-soluble salts thereof are particularly the ammonium salt and the alkali salts such as the sodium or potassium salt; amine salts, too, are suitable.

So-called conditioning shampoos are known and on the market since a long time. They normally contain anionic surfactants, particularly alkyl sulfates and alkyl ether sulfates, and polymer conditioning agents in an aqueous medium.

While these shampoos present good lathering properties, the intensity of the hair conditioning effect achieved thereby very often is not satisfactory; and also the skin mildness of these shampoos is not optimal.

SUMMARY OF THE INVENTION

It has been tried to overcome these disadvantages by using other anionic surfactants, e.g., sulfosuccinates or polyether carboxylic acids and the water-soluble salts thereof, however, this has not led to optimal results either.

By using alkyl amidoether carboxylic acids of the kind described above, a shampoo is obtained which presents an optimal result in respect of lathering properties as well as skin mildness and satisfying conditioning effect.

A part of the surfactant used herein, i.e. 1% to 25% by wt., calculated to the total composition, shall comprise customary anionic surface-active substances, i.e. surfactants of the sulfonate and (or) sulfate type.

Suitable anionic surfactants are particularly the well-known $C_{10-C18}$-alkyl sulfates, and especially the corresponding ether sulfates, e.g., alkyl ether sulfates, particularly $C_{12}$-$Cl_4$-lauryl ether sulfate having 1 to 4 ethylene oxide groups in the molecule, furthermore monoglyceride sulfates, fatty acid amide sulfates obtained by ethoxylation and subsequent sulfation of fatty acid alkanolamides and the alkali salts thereof, in a proportion of preferably 5% to 20% by wt. of the hair shampoo.

Other suitable anionic surfactants within the scope of the invention are α-olefin sulfonates or the salts thereof and particularly also alkali salts of sulfosuccinic acid semiesters, e.g. the disodium salt of monooctyl sulfosuccinate and alkali salts of long-chain monoalkyl ethoxysulfosuccinates, e.g., disodium lauryl ether sulfosuccinate, which are particularly preferred within the scope of the invention.

It is also advisable to use mixtures of several anionic surfactants, e.g., a mixture of an α-olefin sulfonate and a sulfosuccinate, preferably in a ratio of 1:3 to 3:1, particularly about 1:1.

Protein fatty acid condensation products of basically known structure, particularly in a proportion between about 0.5% and 5%, preferably 1% to 3% by wt., of the total liquid shampoo composition are also suitable in admixture with other anionic surfactants.

The weight proportion of alkyl amidoether carboxylic acid: sulfate and (or) sulfonate in the shampoo compositions according to the invention is preferably from 1:5 to 5:1, particularly 1:2 to 2:1, e.g. 1:1.5 to 1:1.

In addition to these essential ingredients a) and b) other anion-active surfactants may be incorporated into the shampoo compositions according to the invention.

A survey of anionic surfactants used in liquid shampoos is listed in the monography of K. Schrader, "Grundlagen und Rezepturen der Kosmetika", 2nd Ed., (1989, Hüthig Buchverlag Heidelberg), pp. 683 to 691.

The preferred total quantity of anionic surfactants in liquid shampoos according to the invention is between 5% and 30% by wt., especially 7,5% to 25%, particularly about 10% to about 20% by wt., calculated to the total composition.

Another essential ingredient of the hair shampoo according to the invention are 0.1% to 10% by wt., preferably about 0.5% to about 7.5% by wt., particularly about 2.5% to about 5% by wt., calculated to the total composition, of a compound selected from the group of $C_8$–$C_{18}$-acyl mono- and dialkanolamides, surface-active betaines and sulfobetaines and (or) surface-active amine oxides.

Suitable long-chain fatty acid mono- and dialkanolamides are, e.g., coconut fatty acid mono- and diethanolamide, myristic fatty acid mono- and diethanolamide, lauric acid mono- and di-ethanolamide as well as -monoisopropanol amide, lauric/myristic acid mono- and -dialkanolamide.

Surface active amine oxides are, e.g., $C_{12}$–$C_8$-alkyl dimethyl amine oxides, e.g., lauryl dimethyl amine oxide, $C_{12}$–$C_8$-alkyl amidopropyl or -ethyl amine oxides, $C_{12}$–$Cl_8$-alkyl di-(hydroxyethyl) or -(hydroxypropyl) amine oxides, or also amine oxides having ethylene oxide and (or) propylene oxide groups in their alkyl chain.

Suitable betaines and sulfobetaines are particularly fatty acid amidoalkyl betaines and sulfobetaines, for instance lauryl hydroxy sulfobetaine.

In detail, betaines may be used of the structures

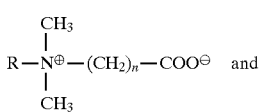

and

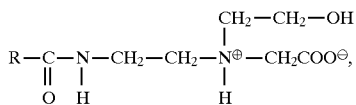

wherein R denotes a $C_8$–$C_{18}$-alkyl group, and n is 1 to 3, sulfobetaines of the structure

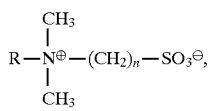

wherein R denotes a $C_8$–$C_{18}$-alkyl group, and n is 1 to 3., and amidoalkyl betaines of the structure

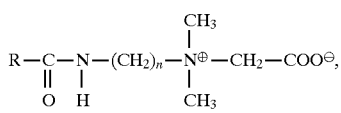

wherein R denotes a $C_8$–$C_{18}$-alkyl group, and n is 1 to 3.

The additional use of other nonionic and amphoteric surfactants is possible.

Those are particularly alkyl polyglucosides of the general formula

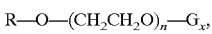

$$R-O-(CH_2CH_2O)_n-G_x,$$

wherein R denotes an alkyl group with 8 to 18 carbon atoms, G is a sugar residue with 5 to 6 carbon atoms, n is a number from 0 to 10, and x is a number between 1.2 and 2.5.

These alkyl polyglucosides have become known recently because of their particular skin mildness and excellent foaming power in liquid shampoos and body cleansing compositions.

Mixtures of anionic surfactants with alkyl polyglucosides and their use in liquid shampoos are known per se, e.g. from European Patent No. 70,074.

The alkyl polyglucosides disclosed therein are basically also suitable within the scope of this invention, as well as the mixtures of sulfosuccinates and alkyl polyglucosides described in European Patent Application No. 358,216.

The fourth essential ingredient of the shampoo according to the invention are cationic polymers, preferably in a quantity between 0.05 and 5%, particularly 0.1% to 2.5%, optimally 0.25% to 1.5% by wt., of the total composition. European Patent Application No. 337,354 describes the use of cationic polymers together with alkyl polyglucoside surfactants; the cationic polymers listed therein on pp. 3 to 7 are also suitable as conditioning additives in the compositions according to the invention.

Particularly preferred within the scope of the invention are cationic polymers having a charge density of at least 2.50 milli-equivalents per gram (meq/g), especially those with a charge density of at least 3.50/meq/g, optimally 4.50 meq/g and more.

In fact, it has surprisingly been found that the combined use of alkyl amidoether carboxylic acids and cationic polymers of higher charge density results in an increased hair conditioning effect of the appropriate shampoo which is not observed when using customary anion-active surfactants alone.

On the other hand, when using polymers of lower charge density, the effect is not so pronounced, but still corresponds at least with that of optimally formulated customary conditioning shampoos. Nevertheless, the combination of alkyl amidoether carboxylic acids and cationic polymers according to the invention produces a satisfactory conditioning effect while maintaining the beneficial properties caused by alkyl amidoether carboxylic acids.

Particularly suitable cationic polymers with appropriate charge densities are dimethyl diallylammonium halide homo- and -co-polymers, especially polydimethyl diallyl ammonium chloride (Polyquaternium-6), and vinyl and methylvinyl imidazolium/vinyl pyrrolidone copolymers (Polyquaternium-16).

The charge densities of the cationic polymers may be calculated from the number of the ionizable nitrogen atoms per mole weight of a monomer unit. The number of the nitrogen atoms may be analytically determined according to the well-known Kjeldahl method.

The liquid hair shampoos according to the invention may additionally contain all ingredients normally used in such preparations.

Examples for such additives are complexing agents, dyestuffs, preservatives, pH-regulants, viscosity controllers such as inorganic salts unless they are already incorporated in the basic surfactant mixtures, fragrances, pearl gloss agents, thickeners, humectants, plant and animal oils such as jojoba oil, etc.

A list of these additives may also be found in Schrader, l. c., pp. 695–722.

Further suitable additives are the well-known protein hydrolyzates, e.g., in a quantity of 0.25% to 5% by wt., preferably 0.5% to 2.5% by wt., of the total composition.

Other suitable conditioning additives are water-soluble collagen or water-soluble collagen derivatives.

DETAILED DESCRIPTION OF THE INVENTION

The following Examples illustrate the invention in detail.

EXAMPLE 1

| | |
|---|---|
| Cocoamidopolyether carboxylic acid (3–4 EO units), sodium salt | 8.00 (% by wt.) |
| Disodium lauryl ether sulfo-succinate (1–4 EO units) | 8.00 |
| α-$C_{14}$–$C_{16}$-Olefin sulfonate | 6.00 |
| Cocoamidopropyl betaine | 3.00 |
| $C_{12}$–$C_{14}$-Alkyl polyglucoside (P.D. ~ 1.5) | 1.00 |
| Lauryl hydroxysultaine | 0.50 |
| Lauryl dimethyl amine oxide | 0.50 |
| Polyquaternium-6 (polydiallyl dimethyl ammonium chloride, charge density ~ 6 meq/g) | 0.80 |
| Polyethyleneglycol-12 | 1.00 |
| Polyethyleneglycol-15 glyceryl isostearate | 0.30 |
| Wheat protein hydrolyzate | 0.40 |
| Polyethyleneglycol-60 hydrogenated castor oil | 0.60 |
| Preservatives | 0.25 |
| Citric acid | 0.20 |
| Perfume | 0.70 |
| Dyestuff | q.s. |
| Water | @ 100.00 |

A mild, transparent shampoo creating an excellent conditioning effect was obtained.

A replacement of the cocoamido polyether carboxylate by the same quantity of sodium laurylether sulfate (2–4 EO units) resulted in a product with a clearly reduced conditioning effect.

EXAMPLE 2

| | |
|---|---|
| Lauryl amidoether carbocylic acid (3–4 EO), sodium salt | 6.00 (% by wt.) |
| Disodium lauryl ether sulfosuccinate | 8.00 |
| α-$C_{14}$–$C_{16}$-Olefin sulfonate | 6.00 |
| $C_9$–$C_{11}$-Alkyl polyglucoside (P.D. ~ 1.4) | 1.00 |
| Cocoamidopropyl betaine | 3.00 |
| Lauryl hydroxy sultaine | 0.50 |
| Lauryl dimethyl amine oxide | 0.50 |
| Polyquaternium-16 (copolymer of methyl vinyl imidazolium chloride/vinyl pyrrolidone; charge density: ~ 6.5 meq/g) | 0.60 |
| Polyethyleneglycl-3 distearate | 3.00 |
| Wheat protein hydrolyzate | 0.50 |
| Polyoxyethylene-160 sorbitan tristearate | 0.30 |
| Polyethyleneglycol-15 | 1.00 |
| Plant extracts | 4.00 |
| Citric acid | 0.20 |
| Preservatives | 0.25 |
| Perfume | 0.60 |
| Dyestuff | q.s. |
| Water | @ 100.00 |

This shampoo showed a distinctly improved conditioning effect in respect of volume, shine, bounce as well as wet and dry combability compared to a customary market product.

A replacement of Polyquaternium-16 by the same quantity of a cationic polymer having a charge density of about 0.4 meq/g (Jaguar CP-13®) resulted in a diminished conditioning effect.

EXAMPLE 3

| | |
|---|---|
| $C_{12}$–$C_{14}$-Alkyl amidoether carboxylic acid (3–4 EO-units), sodium salt | 8.00 (% by wt.) |
| Disodium lauryl ether sulfosuccinate | 5.00 |
| Sodium lauryl ether sulfate (2–4 EO) | 4.50 |
| $C_{12}$–$C_{14}$-Alkyl polyglucoside (P.D. ~ 1.55) | 3.00 |
| Lauryl hydroxyysultaine | 0.50 |
| Coconut fatty acid monoethanolamide | 0.75 |
| Polyquaternium-6 | 0.50 |
| Wheat protein hydrolyzate | 0.30 |
| Polyoxyethylene-160 sorbitan tristearate | 0.30 |
| Polyoxyethyleneglycol-60 hydrogenated castor oil | 0.70 |
| Preservatives | 0.25 |
| Perfume | 0.80 |
| Citric acid | 0.15 |
| Water | @ 100.00 |

A mild, transparent, well-lathering shampoo with an excellent conditioning effect on the hair was obtained.

EXAMPLE 4

| | |
|---|---|
| Cocoamidoether carboxylic acid (2–4 EO units), sodium salt | 8.00 (% by wt.) |
| Disodium lauryl ether sulfosuccinate | 8.00 |
| Lauryl hydroxysultaine | 0.30 |
| Cocoamidopropyl betaine | 2.80 |
| $C_9$–$C_{11}$-Alkyl polyglucoside (P.D. ~ 1.4) | 2.00 |
| Glyceryl caprate | 1.10 |
| Polyquaternium-6 | 0.40 |
| Polyquaternium-7 (charge density ~ 4.3 meq/g) | 0.40 |
| Polyoxyethylene-160 sorbitan tristearate | 1.00 |
| Polyethyleneglycol-60 hydrogenated castor oil | 0.50 |
| Plant extract | 0.50 |
| Octopirox ® (Piroctone Olamine) | 0.45 |
| Perfume | 0.25 |
| Preservatives | 0.10 |
| Dyestuff | q.s. |
| Water | @ 100.00 |

An anti-dandruff shampoo was obtained having excellent hair conditioning properties.

By way of comparison, the replacement of sodium cocoamidoether carboxylate by the same quantity of sodium lauryl ether sulfate resulted in a noticeable decrease of shine, touch, volume, and wet and dry combability of the shampooed hair.

EXAMPLE 5

| | |
|---|---|
| Lauryl amidoether carboxylic acid (1–2 EO units), sodium salt | 3.00 (% by wt.) |
| α-$C_{14}$–$C_{16}$-Olefin sulfonate | 3.00 |
| Sodium alkyl ether sulfate (2–4 EO units) | 3.00 |
| $C_9$–$C_{11}$-Alkyl polyglucoside (P.D. ~ 1.4) | 4.50 |
| Cocoamidopropyl betaine | 2.80 |
| Lauryl hydroxysultaine | 0.50 |
| Glyceryl caprate | 1.00 |
| Laurylalcohol polyglycol ether (Laureth-16) | 4.50 |
| Polyquaternium-6 | 0.70 |
| Polypropyleneglycol-9 | 1.00 |
| Polyethyleneglycol-60 hydrogenated castor oil | 1.00 |
| Polyglycerol-3 diisostearate | 0.50 |
| Preservatives | 0.25 |
| Perfume | 0.40 |
| Citric acid | 0.20 |
| Water | @ 100.00 |

This shampoo was highly skin-compatible and well-latering, having an excellent hair conditioning effect.

We claim:

1. Aqueous hair shampoo composition containing a combination of a) 1% to 25% by wt. of at least one alkyl amidoether carboxylic acid of formula I

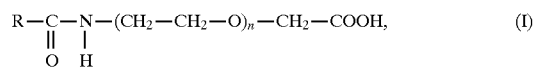

$$R-\underset{\underset{O}{\|}}{C}-\underset{\underset{H}{|}}{N}-(CH_2-CH_2-O)_n-CH_2-COOH, \quad (I)$$

wherein R denotes an alkyl group having 8 to 18 carbon atoms, and n is a number between 1 and 10, and (or) water-soluble salts thereof;

b) 1% to 25% by wt. of at least one anionic sulfate or sulfonate surfactant;

c) 0.1% to 10% by wt. of at least one compound selected from the group of $C_8$–$C_{18}$-acylmono- and-dialkanolamides, surface-active betaines and sulfobetaines and (or) surface-active amine oxides; and d) 0.05% to 5% by wt. of at least one cationic polymer, wherein said cationic polymer has a charge density of at least 2.50 meq/g. all percentages calculated to the total shampoo composition.

2. Shampoo according to claim 1, wherein R denotes an alkyl group having 12 to 14 carbon atoms.

3. Shampoo according to claim 1, wherein n is a number between 2.5 and 5.

4. Shampoo according to claim 3, wherein n is 3 to 4.

5. Shampoo according to claim 1, wherein the anionic surfactant comprises one or more of a sulfosuccinate, an olefin sulfonate and alkyl ether sulfate.

6. Shampoo according to claim 1, wherein the cationic polymer has a charge density of at least 3.50 meq/g.

7. Shampoo according to claim 6, characterized in that it contains a cationic polymer having a charge density of at least 4.50 meq/g.

8. Shampoo according to claim 1, characterized in that it contains a dimethyl diallyl ammonium chloride homopolymer or copolymer.

9. Shampoo according to claim 1, characterized in that it contains a vinyl or methyl vinyl imidazolium chloride/vinyl pyrrolidone copolymer.

* * * * *